(12) United States Patent
Mahalingam et al.

(10) Patent No.: US 8,264,246 B2
(45) Date of Patent: Sep. 11, 2012

(54) ELECTRICAL NETWORK REPRESENTATION OF A DISTRIBUTED SYSTEM

(75) Inventors: Sakethraman Mahalingam, Bangalore (IN); Manoj Kumar Koyithitta Meethal, Bangalore (IN); Arijit Banerjee, Bangalore (IN); Wrichik Basu, Bangalore (IN); Harish Kumar Pillai, Mumbai (IN)

(73) Assignee: General Electric Company, Niskayuna, NY (US)

( * ) Notice: Subject to any disclaimer, the term of this patent is extended or adjusted under 35 U.S.C. 154(b) by 433 days.

(21) Appl. No.: 12/652,116

(22) Filed: Jan. 5, 2010

(65) Prior Publication Data

US 2011/0163770 A1 Jul. 7, 2011

(51) Int. Cl.
*G01R 27/08* (2006.01)
(52) U.S. Cl. .................. 324/693; 324/691
(58) Field of Classification Search ............ 324/693, 324/691
See application file for complete search history.

(56) References Cited

U.S. PATENT DOCUMENTS

| | | | |
|---|---|---|---|
| 4,063,153 | A | 12/1977 | Dechene et al. |
| 4,975,645 | A | 12/1990 | Lucas |
| 5,291,791 | A | 3/1994 | Lucas et al. |
| 5,396,806 | A | 3/1995 | Dechene et al. |
| 7,167,009 | B2 | 1/2007 | van Schoor et al. |
| 7,496,450 | B2 * | 2/2009 | Ortiz Aleman et al. ......... 702/6 |
| 8,027,794 | B2 * | 9/2011 | Xie ............................. 702/50 |
| 2003/0085715 | A1 | 5/2003 | Lubkeman et al. |
| 2006/0265150 | A1 | 11/2006 | Hu et al. |

OTHER PUBLICATIONS

Mohd. Zaid Abdul L Ah; "Simulation of an Inverse Problem in Electrical Impedance Tomography Using Resistance Electrical Network Analogues"; Int. J. Elect. Enging. Educ., vol. 36, pp. 311-324. Manchester U.P., 1999. Printed in Great Britain.

J. H. Calderwood and E. R. Mognaschi; "A novel field for possible use in medical impedance tomography"; Journal of Medical Engineering & Technology, 1998, vol. 22, No. 3, pp. 121-125.

Jun Gu, W Yin, Yannian Rui, Chao Wang, Huaxiang Wang; "A New Resistor Network Based Forward Model for Electrical Impedance Tomography Sensors"; I2MTC 2009—International Instrumentation and Measurement, Technology Conference, Singapore, May 5-7, 2009; 4 Pages.

W.Q.Yang et al., "Development of Capacitance Tomographic Imaging Systems for Oil Pipeline Measurements", Review of Scientific Instruments, AIP, vol. 66, No. 8, pp. 4326-4332, Aug. 1995.

J.A. Kjell et al., "Comparison of Different Measurement Protocols in Electrical Capacitance Tomography using Simulations", IEEE Transactions on Instrumentation and Measurements, vol. 56, No. 6, pp. 2119-2130, Dec. 2007.

M.S.Rocha et al., "Void Fraction Measurement and Signal Analysis from Multiple-Electrode Impedance Sensors", Heat Transfer Engineering, vol. 29, pp. 924-935, Jan. 2008.

C-N Huang et al., "Rotational Electrical Impedance Tomography", Measurement Science and Technology, vol. 18, pp. 2958-2966, Aug. 2007.

European Search Report From corresponding Application No. EP10196638, mailed on Apr. 4, 2011.

* cited by examiner

*Primary Examiner* — Amy He
(74) *Attorney, Agent, or Firm* — Ann M. Agosti (57) ABSTRACT

A method for determining characteristics of a multi-material object is provided. The method includes producing a rotating electric field by providing an applied electrical signal set of individual electrical signal patterns to electrodes surrounding the multi-material object. The method also includes obtaining a measured electrical signal of electrical signals from the electrodes corresponding to each electrical signal pattern applied. An electrical network is determined based on the applied electrical signal set, the measured electrical signal set and an inverse of the applied electrical signal set. The method further includes determining the characteristics of the multi-material object by analyzing the electrical network.

25 Claims, 6 Drawing Sheets

ELECTRICAL NETWORK REPRESENTATION OF A DISTRIBUTED SYSTEM

BACKGROUND

This invention relates generally to a method for determining the composition and characteristics of the individual materials in a multi-material object, and, specifically, to a representation and analysis of the multi-material object as an electrical network.

Electrical impedance tomography (EIT) is a minimally invasive measurement technique that can be used to quantitatively map material distributions within multi-material objects. In EIT, a map of the electrical conductivity and permittivity is used to infer the distributions of different materials within that object. Different current patterns or voltage patterns are applied to the object through electrodes surrounding the object, and the corresponding voltages or currents are measured. Based on the current-voltage relations, the internal impedance or internal admittance distribution is determined.

One example of a multi-material object is multiphase flow in which at least two materials or phases are flowing together inside a pipe or a conduit. Multiphase flow processes are important to a variety of industries including, for example, petroleum, pharmaceutical, food, and chemical industries. There is a need for direct knowledge of the internal characteristics in these types of multiphase flow processes to enable improved design and increased operational efficiency of existing and new processing equipment. Characteristics used to predict performance of multiphase processes may include, for example, spatial distribution of the phases (spatial volumetric phase fractions), flow regime, interfacial area, and absolute and relative velocities between the phases or materials. Knowing the spatial distribution of the materials is particularly useful because non-uniform distribution of the materials tends to reduce the interfacial area between materials available for chemical reaction or conversion and may result in recirculating flows creating spatially non-uniform reaction zones or concentrations. Further, the volumetric phase fraction and velocity are important parameters that enable proper and timely control of multiphase flows.

In one EIT technique, currents are applied to pairs of boundary electrodes, one pair at a time with the current entering at one electrode and leaving at another, and voltages are measured on the all the electrodes. In an analogous technique, voltages are applied to pairs of boundary electrodes, one pair at a time, and currents are measured at all the electrodes. One challenge associated with these techniques is low signal-to-noise ratio. Further, when materials with small variations in relative permittivities or conductivities are involved, the resolution is reduced.

In another EIT technique, currents or voltages are applied to all the electrodes simultaneously to produce the data necessary for a complete measurement. The currents or voltages applied to electrodes are all electrically in phase with each other and have different amplitudes. However, this technique is more time consuming because the number of current or voltage patterns applied to the electrodes is high (typically equal to one less than the number of electrodes).

Therefore, it is desirable to provide a method and a system that will address the foregoing issues.

BRIEF DESCRIPTION

In accordance with an embodiment of the present invention, a method to determining characteristics of a multi-material object is provided. The method includes providing an applied electrical signal set of individual electrical signal patterns to electrodes surrounding the multi-material object to produce a rotating electric field within the multi-material object and obtaining a measured electrical signal set of electrical signals from the electrodes corresponding to each applied electrical signal pattern. The method also includes determining an electrical network based on the applied electrical signal set, the measured electrical signal set, and an inverse of the applied electrical signal set. The method further includes determining the characteristics of the multi-material object by analyzing the electrical network.

In accordance with another embodiment of the present invention, a method for determining an electrical network of a multi-material object is provided. The method includes providing an applied electrical signal set of individual electrical signal patterns to electrodes to produce rotating electrical field. The method also includes obtaining a measured electrical signal set of electrical signals from the electrodes corresponding to each applied electrical signal pattern and determining the electrical network based on the applied electrical signal set, the measured electrical signal set and an inverse of the applied electrical signal set.

In accordance with yet another embodiment of the present invention, a multi-material sensing system is provided. The system includes a power supply for providing an applied electrical signal set of individual electrical signal patterns to electrodes surrounding a multi-material object to product a rotating electric field inside the object and a measurement unit for obtaining a measured electrical signal set of electrical signals from the electrodes corresponding to each applied electrical signal pattern. The system further includes a processing circuitry to estimate characteristics of the multi-material object based on the applied electrical signal set, the measured electrical signal set and an inverse of the applied electrical signal set.

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

As discussed in detail below, embodiments of the present invention function to provide a system and a method for measuring characteristics of a multi-material object. In an example of a multiphase flow, the characteristics of the object may include volumetric fractions and flow rates of oil, water, and gas (in this context referencing gaseous hydrocarbons) flowing through conduits. Although the invention is described with reference to a use in oil/gas/water measurements, it is by no means limited to such applications; rather, aspects of the invention find application in a wide variety of industrial, healthcare and chemical processes such as, for example, cancer diagnosis and water treatment processes. The characteristics of such multi-material objects may be quite different from the examples given for multiphase flow.

Figure 1:
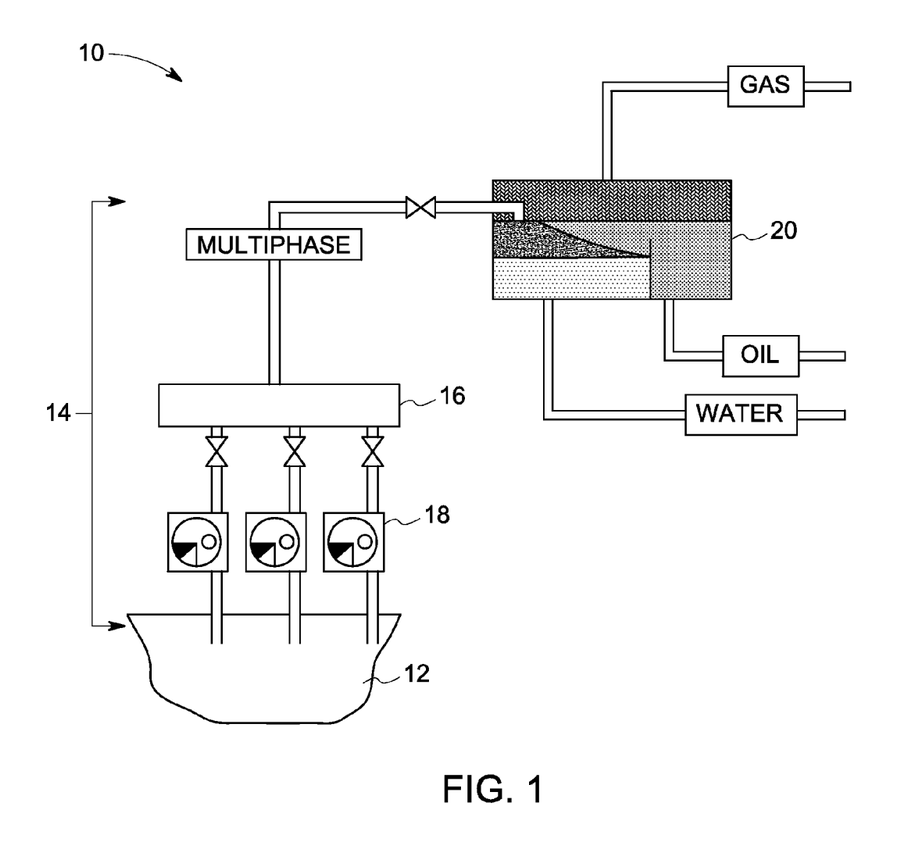
FIG. 1 is a block diagram of a oil production facility according to an example embodiment.

FIG. 1 shows an oil production facility 10 according to an example embodiment. The oil production facility typically includes multiple oil wells 12 that are each interconnected to a piping system 14. The piping system 14 includes a production manifold 16 coupled to multiphase flow meters (MPFMs) 18. A multiphase flow meter enables measurement of unprocessed well streams very close to the well and thus can provide continuous monitoring of well performance, which may be used for better reservoir management. Fluids pumped from oil wells 12 are sent to a production separator 20 through the production manifold 16. It should be noted that a test separator (not shown) may additionally be used along with MPFMs in the facility 10 or may alternatively be used. One advantage of a MPFM over a test separator is the reduction in time needed to perform a measurement. While the test separator must be allowed to fill and stabilize when changing wells, the MPFM responds more quickly to changes in well fluids and needs less time to stabilize.

The production separator 20 separates oil, gas, and water pumped from the wells. The production separator 20 may include one or more measurement devices. The measurement devices may include, for example, a water meter to measure an amount or rate of water extracted from a well and an emulsion meter to measure an amount of oil extracted from the well. Further measurement devices may include other devices typically utilized to monitor well performance such as a wellhead pressure sensor, thermometer, salinity meter and a pH meter.

Figure 2:
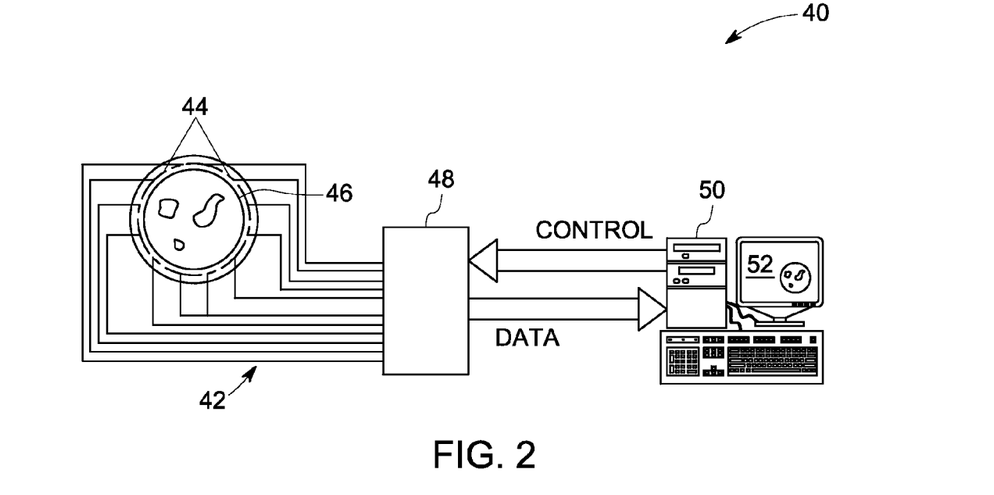
FIG. 2 is a schematic of an electrical impedance tomography (EIT) based multiphase flow meter to be used in accordance with an embodiment of the present invention.

FIG. 2 shows an electrical impedance tomography (EIT) based MPFM system 40. In EIT, the conductivity or permittivity distribution within a multi-material object is inferred from electrical measurements made through electrodes surrounding the object. Conducting electrodes are attached to the periphery of the multi-material object and alternating currents or voltages are applied to some or all of the electrodes. The resulting electrical potentials or currents are measured, and the process is repeated for different configurations or patterns of applied currents and/or voltages.

The MPFM system 40 of FIG. 2 includes an electrode array 42 comprising a number of electrodes 44 distributed around a conduit 46. The conduit may comprise a container, which carries multiple materials or phases within it, such as a pipe or tank or this may comprise another vessel such as a part of a human body or an entire human body. In a more specific embodiment, the number of electrodes may be eight, twelve or sixteen, depending on the size of the conduit and the accuracy needed. The electrodes may be attached directly to inside wall of the conduit with one embodiment including use of a suitable coating to ensure good electrical contact, if needed. An appropriate electrically insulating material may be provided between the electrode and the conduit wall. The electrodes are connected to electronic conditioning circuitry 48 which may include components such as current or voltage sources, D-to-A-converters, A-to-D converters, differential amplifiers, filters, digital multiplexers, analog multiplexers, a clock, and/or a digital I/O unit coupled to a computer 50. Computer 50 comprises, in one embodiment, a personal computer equipped with a digital signal processor card used for the image reconstruction process and a suitable display 52 for displaying the images. Other processing circuits such as a field-programmable gate array (FPGA) or a complex programmable logic device (CPLD) may also be used in other embodiments. In accordance with an embodiment of the present invention, electrodes 44 are stimulated by applying a voltage set of voltage patterns across them, which produces a rotating electric field within the multi-material object in the conduit. At any given time, one or more voltage sources are used to apply one pattern of voltages to the electrodes, and the corresponding set of current signals in each of the electrodes is measured. In one embodiment, instead of applying voltages, one or more current sources are used to stimulate the electrodes by injecting currents into them, and corresponding voltages are measured across the electrodes.

Figure 3:
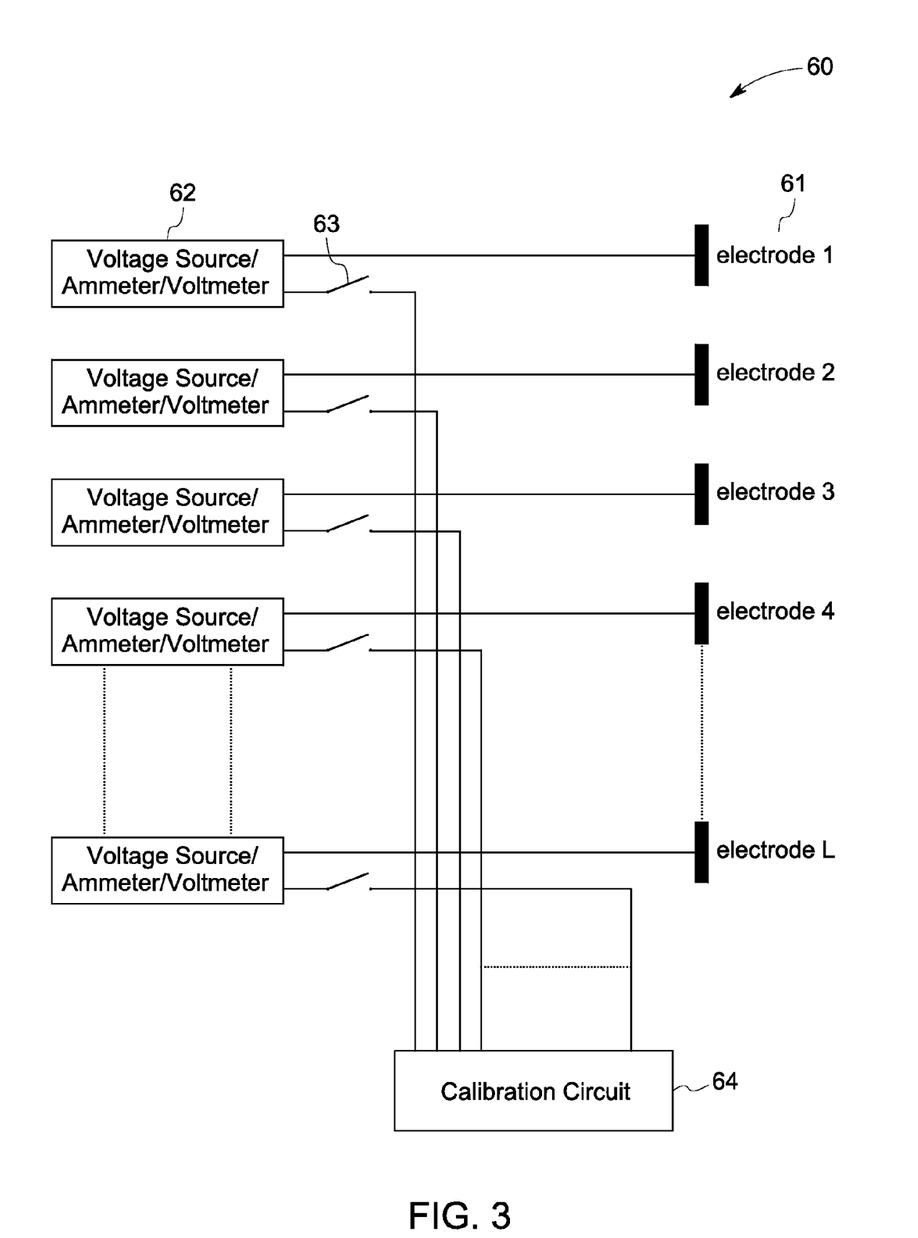
FIG. 3 is a block diagram of an applied-voltage EIT system in accordance with an embodiment of the present invention.

FIG. 3 is a block diagram 60 of an applied-voltage EIT system with L electrodes. Each electrode 61 is connected to a circuit that includes a voltage source 62 for generating the applied voltage as well as an ammeter to measure the current and a voltmeter to directly measure the applied voltage. A switching network 63 enables a single calibration circuit 64 to be connected to any of the voltage source/ammeter/voltmeter circuits to allow the whole system to be calibrated to a single reference. A digital controller (not shown) may be interfaced to the voltage sources (with ammeters and voltmeters), switches, and the calibration circuit sets the system configuration and collects digital measurements of voltage and current. In another embodiment wherein currents instead of voltages are applied to the electrodes, the currents are generated using current sources, which may comprise direct current sources or a system of voltage-to-current converters, for example.

In both of the current and voltage source embodiments, the resulting measurements are processed by the computer 50 (FIG. 2), and the representation of the electrical impedance or admittance distribution within the multi-material object is determined. The electrical impedance or admittance distribution is then further analyzed by the computer 50 to provide characteristics of the multi-material object. Characteristics of the multi-material object may include, for example, composition and distribution of materials of the system. Further, the electrical impedance or admittance distribution may also be analyzed to determine flow regimes, phase fraction, and velocity of individual materials of the multi-material object. The flow regimes may include but are not limited to bubbly flow, churn flow, slug flow, or annular flow, for example.

In voltage source embodiments, the current flowing from one electrode to another is a function of relative voltages applied across all electrodes and the conductivity and permittivity of the materials present between all the electrodes. For example, the material may be only oil or it may be a mixture of oil and gas. Depending on the materials and their distribution, the impedance or admittance between all the electrodes varies, and the current flowing between electrodes also varies. Thus, from the applied voltage set and the measured current set, the impedance set or impedance matrix of impedances between every pair of electrodes can be calculated. Similarly, from the applied voltage set and the measured current set, the admittance set or admittance matrix of impedances between every pair of electrodes can alternatively or additionally be calculated. Because impedance and admittance are a function of the conductivity and the permittivity of the materials between electrodes, by analyzing the impedance or admittance network, the material distribution and its characteristics may be determined.

The voltage set of voltage patterns produces a rotating electric field within the conduit. A rotating electric field is an electric field, which changes direction at a constant angular rate corresponding to the applied signal frequency or its integer multiples. This is similar to the rotating magnetic field, which is a key principle in the operation of a polyphase alternating-current motor where the rotating magnetic field changes direction at a constant angular rate.

Figure 4:
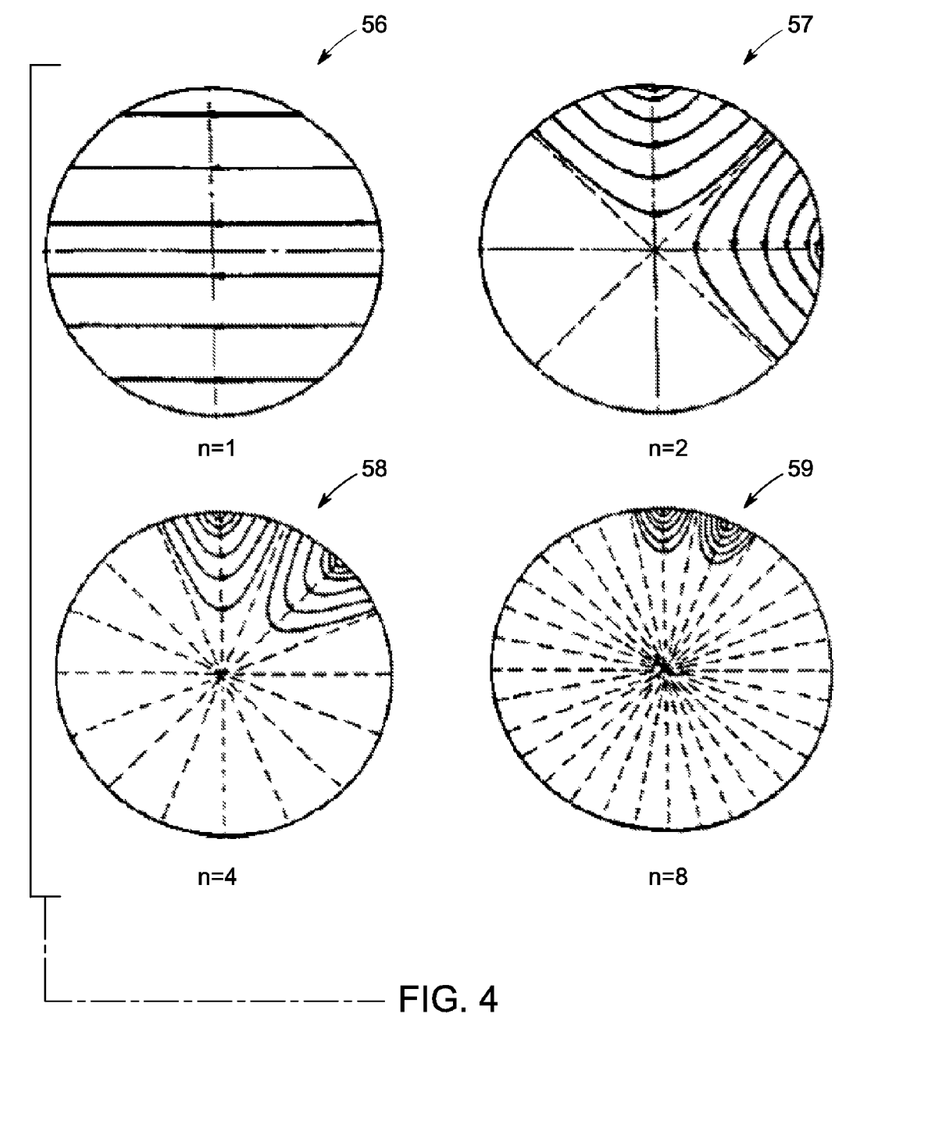
FIG. 4 is a diagrammatical representation of rotating field patterns in accordance with an embodiment of the present invention.

FIG. 4 shows several example electric fields simulated inside a pipe for various spatial harmonic patterns. Plots 56, 57, 58 and 59 represent electric fields for first, second, fourth, and eighth harmonics respectively. For the first harmonic pattern, the electric field consists of parallel straight lines, for the second harmonic pattern, the electric field consists of a family of rectangular hyperbolae, for fourth and eighth harmonic patterns the electric field line curves, while not being hyperbolae, have some resemblance to them.

A rotating electric field may be produced by applying a voltage set of voltage patterns to the electrodes. Assuming L number of electrodes across the pipe, the voltage pattern that will be applied across the electrodes can be represented as:

$$V_k^\lambda = \hat{V}\sin\left(\omega t \pm \frac{2\pi\lambda}{L}(k-1)\right) \quad (1)$$

$$V_k^\lambda = \hat{V}\sin\omega t \cos\left(\frac{2\pi\lambda}{L}(k-1)\right) + \hat{V}\cos\omega t \sin\left(\frac{2\pi\lambda}{L}(k-1)\right) \quad (2)$$

$$V_k^\lambda = \hat{V}\sin\omega t \cos\left(\frac{2\pi\lambda}{L}(k-1)\right) - \hat{V}\cos\omega t \sin\left(\frac{2\pi\lambda}{L}(k-1)\right) \quad (3)$$

where $V_k^\lambda$ is the voltage applied to the kth electrode in the $\lambda^{th}$ excitation pattern, $\hat{V}$ is a peak applied voltage, t is the time and ω is angular frequency of the sine wave. Equations (2) and (3) refer to expansion of equation (1) with separate + and − relations. Equation (2) is a forward voltage pattern for generating clockwise rotating electric field within the object, whereas equation (3) is a reverse voltage pattern for generating counterclockwise rotating electric field within the object. Each excitation pattern is sequentially applied to the electrodes until a full set of patterns given by equations (1) and (2) is completed. The variable λ that corresponds to the excitation pattern varies from 1 to $N_p$, where $N_p=L/2$ in the case where L is an even number and $N_p=(L-1)/2$ in the case where L is an odd number. In one embodiment, for an electrical resistance tomography (ERT) a total of $N_p$ forward voltage patterns or $N_p$ reverse voltage patterns are applied. In another embodiment, both forward and reverse patterns are applied to electrodes to obtain more complete information about the multi-material object. Forward voltage patterns and reverse voltage patterns together provide information about real and imaginary components of electrical elements in the network representation of the multi-material object. In a manner similar to equations (1), (2) and (3), forward current and reverse current patterns can be described and calculated.

Figure 5:
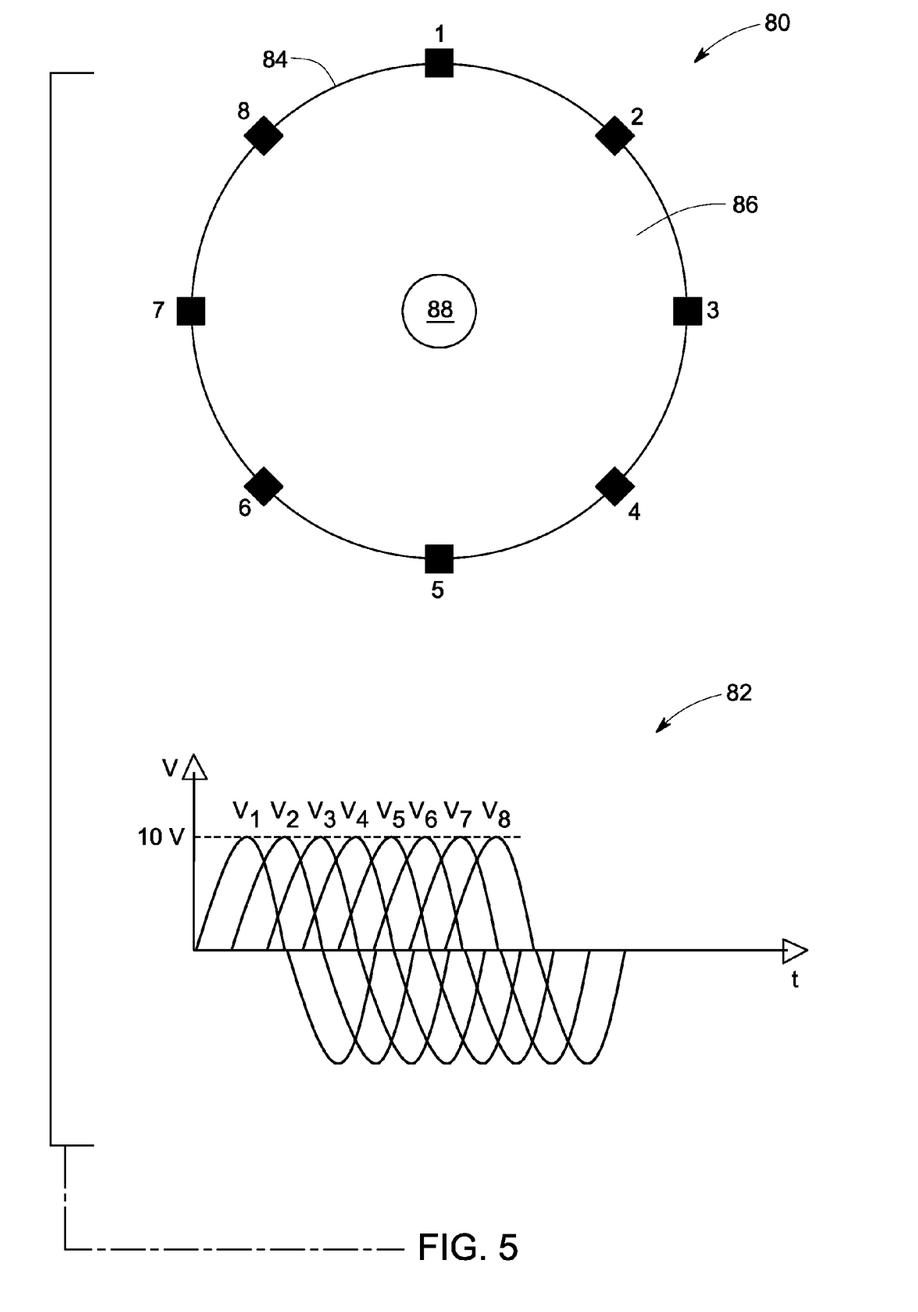
FIG. 5 is a schematic of electrodes surrounding a multi-material object in a conduit and a reference sine waveform in accordance with an embodiment of the present invention.

FIG. 5 shows a schematic 80 of electrodes placed along the periphery of a conduit and a set of waveforms 82 of amplitude V̂=10V. It may be noted that there are 8 sine waveforms that are phase-shifted from each other by an equal extent within the set of waveforms 82. These waveforms are marked V1 to V8 and correspond to the voltage signals applied to the corresponding electrode. For example, V1 corresponds to the voltage signal applied to electrode 1 and V7 refers to the voltage signal applied to electrode 7. The set of waveforms 82 corresponds to one voltage pattern. Several such patterns may be calculated according to equation (1) and be applied to the electrodes. The use of 8 electrodes is for example only, and any other desired number of electrodes may be used. The pipe 84, in one embodiment, includes materials or phases such as oil 86 and water 88.

In an embodiment of the invention, the effect of the permittivity or permeability of some or all the materials that comprise the multi-material object may be known a priori to be of significantly lesser than the conductivity, and, in such cases, the electrical network representing the multi-material object can be said to comprise of only resistive elements. This is a specific case of EIT called as Electrical Resistance Tomography (ERT). In such embodiments where only ERT is to be performed, the total number of voltage or current patterns to be applied to get complete information about the phase distribution is $N_p$. The $N_p$ patterns may be either forward patterns, which produce clockwise rotating electric field, or reverse patterns, which produce counterclockwise rotating electric field.

Figure 6:
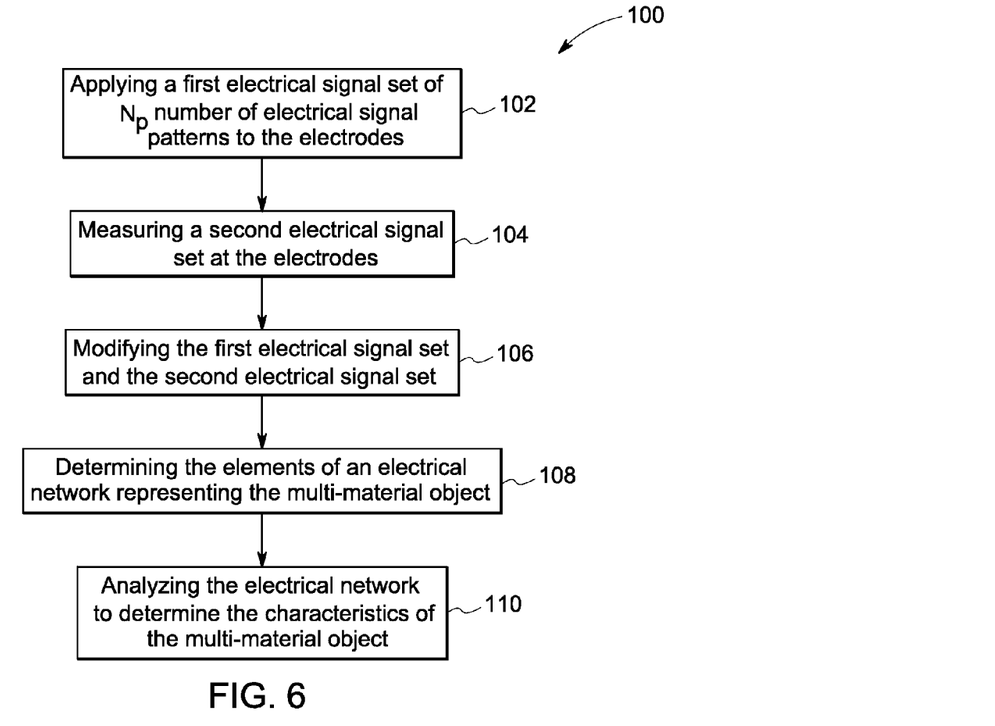
FIG. 6 is a flow chart representing a method of determining the characteristics of a multi-material object using an electrical resistance tomography (ERT) technique according to an embodiment of the present invention.

FIG. 6 shows a method 100 for determining an impedance or admittance matrix in an ERT. In step 102, a first electrical signal set comprising $N_p$ patterns is applied to the electrodes. The corresponding second electrical signal set having a respective second electrical signal pattern for each applied first electrical signal pattern is measured in step 104. In one embodiment, the first electrical signal pattern may comprise a voltage set and the second electrical signal pattern may comprise a current set. In another embodiment, the first electrical signal pattern may comprise a current set and the second electrical signal pattern may comprise a voltage set. In the embodiment wherein the first electrical signal set is a voltage set and the second electrical signal set is a current set, for example, because only $N_p$ voltage patterns are applied to the electrodes, one may construct a voltage matrix representing the applied set of voltage patterns and a current matrix representing the corresponding measured set of current patterns. The voltage and current matrices would have L number of rows and $N_p$ number of columns. The voltage or current at the $m^{th}$ electrode for the $n^{th}$ pattern would be given by element (m,n) of the voltage or current matrix. Further, as an example in the same embodiment, suppose the set of $N_p$ voltage patterns applied are the forward rotating patterns given by equation (2). In the case of L being an odd number, the remaining entries of a voltage matrix can be determined from equation (3) and a resulting new voltage matrix would have L number of rows and L−1 number of columns. In the case of L being an even number, using equation (3) would result in one extra voltage pattern and a new voltage matrix would have L number of rows and L number of columns. It must be noted here that the first pattern computed using equation (3) is effectively the same as the last pattern computed by equation (2), which is the last pattern in the applied voltage set of voltage patterns. Hence, the column corresponding to the first pattern computed using equation (3) may be removed and therefore, a new voltage matrix has L number of rows and L−1 number of columns. Similarly, the remaining entries of a new current matrix may also be determined by using the fact that the individual currents in the measured current pattern resulting from the $i^{th}$ applied voltage signal pattern will be complex conjugate of the current at the same electrode corresponding to the $(L+1-i)^{th}$ current pattern since the elements in the impedance or admittance network are purely resistive in the case of an ERT. Thus, in step 104, the first and second electrical signal matrices are modified.

In step 108, based on the full applied electrical signal set, the resulting full electrical signal set, an inverse of the full applied electrical signal set, and an impedance matrix or an admittance matrix representing the material distribution within the multi-material object is determined. In one embodiment, a pseudo inverse calculation may be utilized to determine the inverse of the applied signal set. The calculated matrix is the electrical network representation of the material distribution within the object. It is a symmetric matrix with complex entries. In other words, the element in the ith row and jth column of a matrix a is equal to the element in the jth row and ith column of the matrix a, for all indices i and j:

$$a_{i,j}=a_{j,i}$$

where $a_{i,j}$ is the equivalent impedance or admittance between electrodes number i and j. The calculated impedance or admittance matrix is then analyzed in step 110 to determine characteristics of the multi-material object. In the admittance matrix, the row sum is zero for every row and the column sum is zero for every column when there is no leakage path for the currents to flow through. This fact may be utilized to detect any current paths present in the system apart from the electrodes and their associated circuits themselves.

Figure 7:
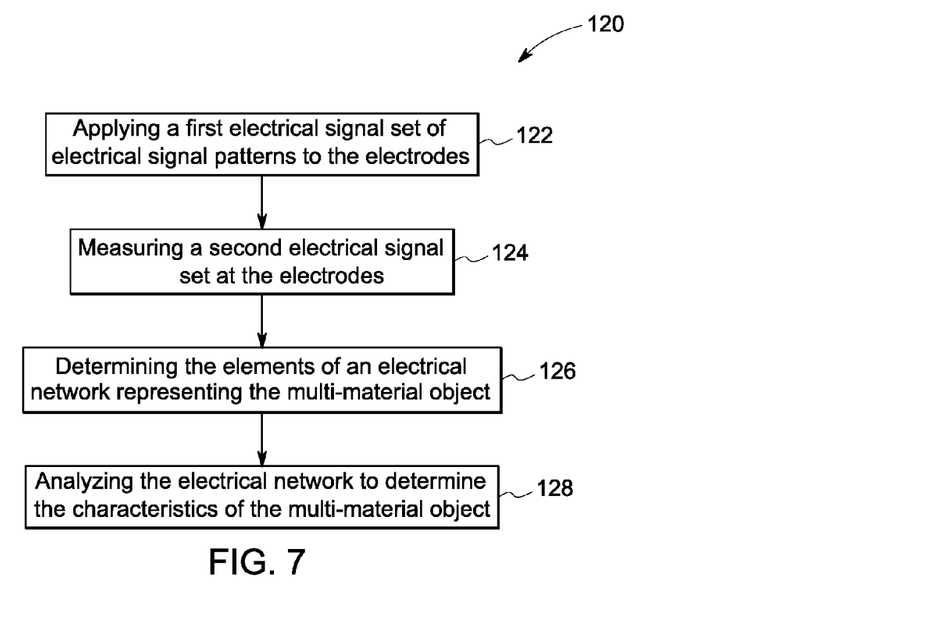
FIG. 7 is a flow chart representing a method of determining characteristics of a multi-material object using an EIT technique according to an embodiment of the present invention.

FIG. 7 shows a method 120 for determining an impedance or admittance matrix in an EIT in a voltage source embodiment. In one embodiment, for an EIT, when the permittivities of the materials within the multi-material object are not known, both the forward voltage patterns and reverse voltage patterns are applied to the electrodes in step 122. In step 124, the resultant current signals are measured from the electrodes. It should be noted that rather than applying voltage patterns, currents patterns can also be applied and voltage patterns might also be measured. The total number of voltage patterns applied is one less than the number of electrodes, since the remaining pattern is effectively redundant. Thus, for L electrodes, the total voltage patterns applied would be L−1. The electrical network is then determined in step 126 based on the first electrical signal set, the second electrical signal set, and the inverse of the first electrical signal set. The electrical network is further analyzed in step 128 to determine characteristics of the multi-material object.

Figure 8:
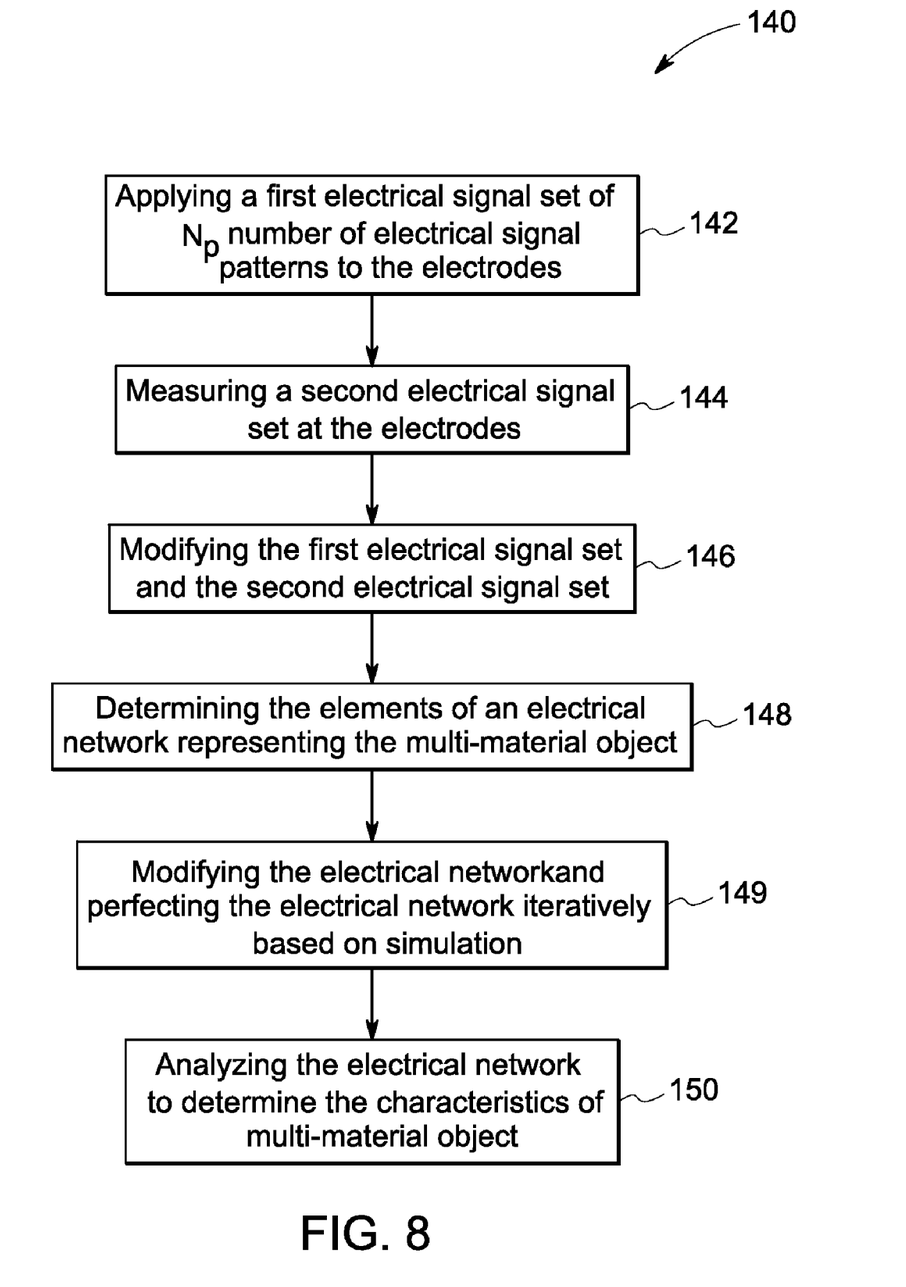
FIG. 8 is a flow chart representing another method of determining characteristics of a multi-material object using an ERT technique of FIG. 6 according to an embodiment of the present invention.

FIG. 8 shows another method 140 for determining impedance or admittance matrix in an EIT. In this embodiment, the ERT procedure as explained in FIG. 6 is first performed. A voltage set of $N_p$ voltage patterns is applied to the electrodes in step 142 and a resultant current set is measured in step 144. In step 146, the voltage set and current set are modified by filling in the remaining half of the matrix as described earlier with respect to FIG. 6 to make them full voltage and current matrices of size (L, L−1). In step 148, based on the applied voltage set, the measured current set, and the inverse of the applied voltage set, an admittance matrix or impedance matrix is determined. Further, based on the value of the purely resistive elements in the electrical network determined by ERT, the conductivities and the distribution of the different materials within the object are estimated using pre-computed results from numerical models and the impedance or admittance matrix which only has purely resistive elements until this step (real numbers in the matrix) is now modified into a new impedance or admittance matrix to have an capacitive or inductive element (complex numbers in the matrix). For example, if the ERT provides three different conductivity values at three different locations within the object, it may be estimated that if the conductivity values is in the range of $10^{-6}$ siemens/meter, then the material is similar to oil and hence the relative permittivity may be in the range of 1 to 5. Similarly if the conductivity values in the range of $10^{-3}$ siemens/meter or above it may be determined that the material is water and hence the relative permittivity may be between 75 and 80. Once the relative permittivity is estimated, the capacitive part of the electrical network elements can be estimated. The new impedance or admittance matrix is then simulated with known applied voltage patterns, and simulated currents are determined. The new electrical network is perfected in step 149 by iteratively minimizing the error between the measured current set and the simulated current set. As explained earlier, the perfected electrical network is then analyzed to determine characteristics of multi-material object in step 150. There may be other ways of estimating the relative permittivity of the materials based on the conductivity values and alternatively or additionally using other sensor information such as for example, using the information from a density meter. Further, there may be prior knowledge of the spatial distribution of the different materials within the multi-material object, such as for example, within the human head. The step 149 uses all such information to suitably modify the impedance or admittance matrix such that capacitive or inductive portions are added to the elements.

The computer 50 (FIG. 2) stores, processes and communicates information regarding applied voltage patterns, measured current signals and the calculated impedance or admittance matrix. The voltage patterns together form a voltage set or applied signal set and the measured currents form a current set or the measured signal set. As described earlier, in another embodiment, the currents may be injected into the electrodes and the voltages may be measured. If the applied signal set is a voltage set and the measured signal set is a current set, then the applied signal set may be represented by a matrix P and the measured signal set may be represented by a matrix Q. The impedance network is then represented by a matrix Z, where $$Z=P*Q^{-1} \quad (4)$$

$Q^{-1}$ refers to the inverse of the matrix Q. However, the matrix Q is a measured signal set and is typically a mathematically ill-posed matrix. Hence it is difficult to find an inverse of this matrix. Thus, calculating an admittance matrix is easier in this case since admittance matrix can be calculated as given below:

$$Y=Q*P^{-1} \quad (5)$$

The applied signal set has better fidelity than the measured signal set. Further, since the applied signal set is known well before hand, it can be stored in the computer and its inverse can also be stored in the computer. Thus, for determining the admittance matrix, the measured signal set is directly multiplied by the available inverse of the applied voltage signal. In one embodiment, the object may also be represented and calculated by an impedance matrix Z, if the applied signal set is a current set M and the measured signal set is a voltage set S. The impedance matrix Z in this case is given by $$Z=S*M^{-1} \quad (6)$$

Again, $M^{-1}$ refers to the inverse of matrix M. Here again calculating the inverse of the applied signal set M is easy as compared to calculating the inverse of measured signal set S.

In both equations (5) and (6), in one embodiment, a pseudo inverse is utilized to calculate inverses of matrices P and M. Pseudo inverse techniques may include, for example, one-sided inverse, Drazin inverse, Group inverse, Bott-Duffin inverse, or Moore-Penrose pseudo inverse. The inverse calculation technique is thus used to obtain a direct calculation of an impedance matrix or an admittance matrix instead of using a numerical method or an iterative method. The admittance matrix Y and impedance matrix Z of equations (5) and (6) may then be calculated as:

$$Y = Q * ((P^H P)^{-1} * P^H) \quad (6)$$

$$Z = S * ((M^H M)^{-1} * M^H) \quad (7)$$

where, $P^H$ and $M^H$ are conjugate transposes of matrices P and M.

In some process systems, admittance or impedance matrix elements in the electrical network representation of a multi-material system may vary with time. However, since the applied signal set is constant and the measured signal set is measured in real time, a time varying admittance matrix or impedance matrix may also be calculated. In one embodiment, various pre-computed tables or matrices of different random flow regime models are stored in the computer and when the system determines the electrical network representation, it is simply compared with stored matrices and thus the flow regime and material distribution within the multi-material object is identified. In another embodiment, the admittance or impedance matrix is analyzed by a heuristic algorithm to determine material distribution and other characteristics of the multi-material object. The heuristic algorithm may include a fuzzy logic algorithm or a genetic algorithm or a neural network algorithm for example. The fuzzy logic algorithm provides a simple way to arrive at a conclusion based upon vague, ambiguous, imprecise, noisy, or missing input information. The results of fuzzy logic algorithm are approximate rather than precise. Further, a neural network may be trained to identify the likeliest material distribution and other characteristics of the object based on the historical behavior of the multi-material object.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A method of determining characteristics of a multi-material object comprising:
    providing an applied electrical signal set of individual electrical signal patterns to electrodes surrounding the object for producing a rotating electric field;
    obtaining a measured electrical signal set of electrical signals at the electrodes corresponding to each applied electrical signal pattern;
    determining an electrical network representation of the object based on the applied electrical signal set, the measured electrical signal set, and an inverse of the applied electrical signal set; and
    determining the characteristics of the multi-material object by analyzing the electrical network.

2. The method of claim 1, wherein the multi-material object comprises oil, water, and gas.

3. The method of claim 1, wherein a maximum number of the individual electrical signal patterns is at most equal to a total number of the electrodes.

4. The method of claim 1, wherein a maximum number of the individual electrical signal patterns is at most equal to one half a number of the electrodes and wherein the electrical network comprises purely resistive elements.

5. The method of claim 4, wherein determining the electrical network comprises converting the applied electrical signal set into a full applied electrical signal set and converting the measured electrical signal set into a full measured electrical signal set.

6. The method of claim 5, wherein converting the applied electrical signal set comprises utilizing known electrical signal patterns.

7. The method of claim 5, wherein converting the measured electrical signal set comprises utilizing the purely resistive nature of the electrical network.

8. The method of claim 1, wherein determining the characteristics comprises determining a new electrical network when a maximum number of the individual electrical signal patterns is at most equal to a one half a number of the electrodes.

9. The method of claim 8, wherein determining the new electrical network comprises modifying the electrical network based on resistance values of the electrical network.

10. The method of claim 9, wherein the new electrical network comprises resistive and capacitive elements.

11. The method of claim 9, wherein the new electrical network comprises resistive and inductive elements.

12. The method of claim 8, wherein determining the characteristics comprises perfecting the new electrical network by simulating it with the applied electrical signal set and minimizing the error between the actual measured electrical signal set and a simulated measured electrical signal set.

13. The method of claim 1, wherein the individual electrical signal patterns comprise spatial harmonic patterns.

14. The method of claim 1, wherein the applied electrical signal set comprises a voltage set and the measured electrical signal set comprises a current set.

15. The method of claim 1, wherein the applied electrical signal set comprises a current set and the measured electrical signal set comprises a voltage set.

16. The method of claim 1, wherein the electrical network comprises time varying elements.

17. The method of claim 1, wherein the inverse of the applied signal set comprises a pseudo inverse of the applied signal set.

18. The method of claim 1, wherein analyzing the electrical network comprises analyzing the electrical network based on a heuristic algorithm.

19. The method of claim 1, wherein characteristics of the multi-material object comprise composition and distribution of different materials within the object.

20. The method of claim 1, wherein determining the characteristics of the multi-material object comprises determining flow regimes and volumetric fraction and velocity of the materials within the multi-material object.

21. The method of claim 1, wherein the electrical network representation comprises an admittance matrix or an impedance matrix.

22. The method of claim 21, wherein the row sum of the admittance matrix is zero for every row and the column sum of the admittance matrix is zero for every column and wherein there is no leakage path for the currents to flow through.

23. A method of determining an electrical network representation of a multi-material object comprising:
    providing an applied electrical signal set of individual electrical signal patterns to electrodes surrounding the object for producing rotating electrical field inside the object;

obtaining a measured electrical signal set of electrical signals at the electrodes corresponding to each applied electrical signal pattern; and determining an electrical network representation of the multi-material object based on the applied electrical signal set, the measured electrical signal set, and an inverse of the applied electrical signal set.

24. A multi-material sensing system comprising:

a power supply to provide an applied electrical signal set of individual electrical signal patterns to electrodes surrounding a multi-material object to produce a rotating electric field;

a measurement unit to obtain a measured electrical signal set of electrical signals at the electrodes corresponding to each applied electrical signal pattern; and processing circuitry to calculate the electrical network representation of the object and to estimate characteristics of the multi-material object based on the applied electrical signal set, the measured electrical signal set, and an inverse of the applied electrical signal set.

25. The method of claim 24, wherein characteristics of the multi-material object comprise composition and distribution of materials within the system.

* * * * *